(12) United States Patent
Yokoyama et al.

(10) Patent No.: US 9,198,892 B2
(45) Date of Patent: *Dec. 1, 2015

(54) COMPOSITION AND/OR METHOD FOR PREVENTING ONSET AND/OR RECURRENCE OF CARDIOVASCULAR EVENTS

(71) Applicant: MOCHIDA PHARMACEUTICAL CO., LTD., Tokyo (JP)

(72) Inventors: Mitsuhiro Yokoyama, Kobe (JP); Hideki Origasa, Toyama (JP); Masunori Matsuzaki, Ube (JP); Yuji Matsuzawa, Takarazuka (JP); Yasushi Saito, Chiba (JP); Yuichi Ishikawa, Kobe (JP); Shinichi Oikawa, Tokyo (JP); Jun Sasaki, Fukuoka (JP); Hitoshi Hishida, Nagoya (JP); Hiroshige Itakura, Tokyo (JP); Toru Kita, Kyoto (JP); Akira Kitabatake, Nara (JP); Noriaki Nakaya, Tokyo (JP); Toshiie Sakata, Fukuoka (JP); Kazuyuki Shimada, Utsunomiya (JP); Kunio Shirato, Sendai (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 445 days.

This patent is subject to a terminal disclaimer.

(21) Appl. No.: 13/672,405

(22) Filed: Nov. 8, 2012

(65) Prior Publication Data

US 2013/0065956 A1    Mar. 14, 2013

Related U.S. Application Data

(63) Continuation of application No. 11/481,956, filed on Jul. 7, 2006, now Pat. No. 8,367,725.

(30) Foreign Application Priority Data

Jul. 8, 2005   (JP) ................................. 2005-200503

(51) Int. Cl.
*A61K 31/232* (2006.01)
*A61K 9/48* (2006.01)

(52) U.S. Cl.
CPC .............. *A61K 31/232* (2013.01); *A61K 9/48* (2013.01)

(58) Field of Classification Search
None
See application file for complete search history.

(56) References Cited

U.S. PATENT DOCUMENTS 6,159,993 A    12/2000 Seed et al.
2003/0100610 A1    5/2003 Shibuya

FOREIGN PATENT DOCUMENTS

EP    1 417 963 A1    5/2004
WO   WO 00/48592 A1    8/2000
WO   WO 02/089787 A1    11/2002

OTHER PUBLICATIONS

Cab et al., Journal of the American College of Cardiology, vol. 45, No. 10, pp. 1723-1728 (2005).
Dehmer et al., "Reduction in the Rate of Early Restinosis After Coronary Angioplasty by a Diet Supplemented with n-3 Fatty Acids," New England Journal of Medicine, Massachusetts Medical Society, vol. 319, No. 12, Sep. 22, 1988, pp. 733-740.
Dictionary definition of the word, "beyond"—The American Heritage Collection Dictionary, 3rd Edition, Houghton Mifflin Co., Boston, MA, 1993, p. 133.
Eritsland et al., The American Journal of Cardiology, vol. 77 ,, pp. 31-36 (Jan. 1996).
European Search Report issued Sep. 14, 2009, in European Patent Application No. 06780884.0.
Johansen et al., Journal of the American College of Cardiology, vol. 33, No. 6, pp. 1619-1626 (May 1999).
Leaf et al., "Do Fish Oils Prevent Restenosis After Coronary Angioplasty?," Circulation (1994), vol. 90, No. 5, pp. 2248-2257.
Maresta et al., American Heart Journal, vol. 143, No. 6, pp. 1-10 (Jun. 2002).
Mulder et al., The American Journal of Cardiology, vol. 86, pp. 742-746 (Oct. 2000).
Nye et al., "Effect of Eicosapentaenoic Acid on Restenosis Rate, Clinical Course and Blood Lipids in Patients After Percutaneous Transluminal Coronary Angioplasty," Australian and New Zealand Journal of Medicine, Royal Australasian College of Physicians, Sydney, AU, vol. 20, No. 4, Jan. 1, 1990, pp. 549-552.
Pharmaceuticals Interview Form, "EPA preparation, Epadel Capsules 300", pp. 21-22 (Jan. 2003).
Ross et al., Arch Intern Med., vol. 159, pp. 1793-1802 (1999).
Serruys et al., JAMA-EXPRESS, vol. 287, No. 24, pp. 3215-3223 (2002).
Shepherd et al., New England Journal of Medicine, vol. 333, No. 20, pp. 1301-1307 (1995).
The Lancet, vol. 344, pp. 1383-1389 (1994).
The Lancet, vol. 354, pp. 447-455 (1999).
von Schacky, "The Role of Omega-3 fatty Acids in Cardiovascular Disease," Current Artherosclerosis Reports (2003), vol. 5, pp. 139-145.
Yamaguchi et al., IGAKUSHOIN, pp. 236-237 and 245-246, 2003.
Yokoyama et al., American Heart Journal, pp. 613-620 (2003).

*Primary Examiner* — Bethany Barham
*Assistant Examiner* — Barbara Frazier
(74) *Attorney, Agent, or Firm* — Birch, Stewart, Kolasch & Birch, LLP

(57) ABSTRACT

Provided are composition and/or methods useful in preventing onset and/or recurrence of cardiovascular events, especially in patients who have escaped the unstable period after cardiovascular angioplasty or in hyperlipidemia patients who have been treated with HMG-CoA RI.

15 Claims, No Drawings

COMPOSITION AND/OR METHOD FOR PREVENTING ONSET AND/OR RECURRENCE OF CARDIOVASCULAR EVENTS

CROSS REFERENCE TO RELATED APPLICATIONS

This application is a 37 C.F.R. §1.53(b) continuation of U.S. application Ser. No. 11/481,956 filed Jul. 7, 2006, which claims the benefit of priority to Japan Patent Application No. 2005-200503, filed on Jul. 8, 2005. The contents of each of these applications is incorporated herein by reference.

TECHNICAL FIELD

This invention relates to compositions and/or methods for preventing onset and/or recurrence of cardiovascular events which contain at least ethyl icosapentate (hereinafter abbreviated as EPA-E).

BACKGROUND ART

Westernization of diet has resulted in the increase of patients suffering from lifestyle-related diseases such as diabetes, hyperlipidemia, and hypertension. Some of these diseases finally lead to arteriosclerotic diseases such as myocardial infarction, angina pectoris, and cerebral infarction and sometimes results in death. As treatment of arteriosclerotic diseases, for example, drugs or surgical methods such as vascular angioplasty are generally utilized.

For prevention of arteriosclerotic diseases or improvement of quality of life, it is important to reduce risk factors such as hyperlipidemia, diabetes, hypertension, and smoking habits. In the major epidemiological survey where incidence rates of hyperlipidemia and coronary artery disease were examined, positive correlation was found between serum total cholesterol (hereinafter abbreviated as T-Cho) concentration or serum triglyceride (hereinafter abbreviated as TG) concentration and the onset of the coronary artery disease. More specifically, even stronger positive correlation was found for the serum low density lipoprotein cholesterol (hereinafter abbreviated as LDL-Cho) concentration, while negative correlation was found for the serum high density lipoprotein cholesterol (hereinafter abbreviated as HDL-Cho) concentration.

Pharmacotherapy of hyperlipidemia has become relatively easy, and suppression of onset of coronary artery diseases by a strong therapy of hyperlipidemia using 3-hydroxy-3-methylglutaryl coenzyme A reductase inhibitor (hereinafter abbreviated as HMG-CoA RI) has been proven in a large scale clinical trial. For example, when male hyperlipidemia patients with no history of myocardial infarction were orally administered with pravastatin sodium for an average period of 4.9 years, serum T-Cho concentration decreased by 20%, serum LDL-Cho concentration decreased by 26%, serum HDL-Cho concentration increased by 5%, and serum TG decreased by 12%, and as a consequence, the total incidence rate of nonfatal myocardial infarction and cardiovascular death decreased by 31% (The New England Journal of the Medicine, 1995, vol. 333, pp. 1301-1307). When patients with history of angina pectoris or myocardial infarction were orally administered with simvastatin for an average period of 5.4 years, serum T-Cho concentration decreased by 25%, and serum LDL-Cho concentration decreased by 35%, serum HDL-Cho concentration increased by 8%, and serum TG decreased by 10%, and as a consequence, the incidence rate of major cardiovascular events decreased by 34% (The Lancet, 1994, vol. 344, pp. 1383-1389). The decrease in the incidence rate of the cardiovascular events was also approximately 20 to 30% in other large scale clinical trials using HMG-CoA RI (Archives of Internal Medicine, 1999, vol. 159, No. 1, pp. 1793-1802). These results may not be sufficient for clinical practice.

It has been reported that when a capsule that includes a ω-3 polyunsaturated fatty acid composition containing EPA-E and ethyl docosahexaenoate (hereinafter abbreviated as DHA-E) in a total amount of 850 to 882 mg was orally administered to patients within three months from the onset of acute myocardial infarction every day for 3.5 years, the combined incidence rate of cardiovascular death, nonfatal myocardial infarction, and nonfatal cerebral infarction decreased by 20%, and that, while cardiovascular death decreased by 30%, no significant effect was observed on nonfatal cardiovascular events (The Lancet, vol. 354, Aug. 7, 1999, pp. 447-455). It was also reported that their death rate decreased when 1 g of essential fatty acids containing EPA-E and DHA-E in a total amount of 85% was administered to patients with history of myocardial infarction every day for 3.5 years (WO 00/48592 (JP 2002-537252 A)). It is also disclosed that the use of EPA or DHA in combination with a cholesterol synthesis inhibitor represses cardiovascular events (U.S. Pat. No. 6,159,993).

High purity EPA-E is commercially available in the trade names of Epadel and Epadel S (manufactured by Mochida Pharmaceutical Co., Ltd.) as the therapeutic drug for hyperlipidemia. It has been reported that when such high purity EPA-E is orally administered at 600 mg per administration and three times a day immediately after meals (when serum TG is abnormal, the dose can be increased to the level of 900 mg per administration and three times a day), serum T-Cho concentration and serum TG can be reduced by 3 to 6% and by 14 to 20%, respectively (Drug Interview Form "EPA preparation, Epadel capsule 300," revised in July, 2002; January, 2003; pp. 21-22), and that based on such action, such high purity EPA-E is expected to exert effects on cardiovascular events of hyperlipidemia patients (American Heart Journal, 2003, vol. 146, No. 4, pp. 613-620).

On the other hand, as an option for treatment of Ischemic heart disease, a surgical treatment, cardiovascular angioplasty such as PTCA, and coronary stent implantation has been widely carried out mainly for serious patients, but cardiovascular events are easy to occur after the angioplasty. For example, the cardiovascular event after PTCA is due to restenosis at the PTCA site, which generally means progression of stenosis in more than 50% of the region expanded by PTCA, or generation of new lesion in many cases. The restenosis rate is approximately 30-40% and the restenosis is usually observed at or within six months. The restenosis rate can be reduced by using stent but it is not always reliable (T. Yamaguchi & M. Kitahara, Kon-nichi no tiryoushishin, published by IGAKUSHOIN, pp. 237, 2003).

As medical treatment with drugs after cardiovascular angioplasty, anti-platelet agents are often used. For example, a combination of aspirin and Ticlopidine (Clopidogrel) is administered as a matter of course when a stent is inserted. For prevention of stent thrombi, a combination of aspirin and cilostazol is administered (T. Yamaguchi & M. Kitahara, Kon-nichi no tiryoushishin, published by IGAKUSHOIN, pp. 245-246, 2003). In particular, care after the surgery is considered important.

Although fish oil or omega-3 fatty acids have been administered to the patients with restenosis in the unstable period after cardiovascular angioplasty, there are controversial reports regarding their efficacy, while there is a view that they have to start to be administered before the cardiovascular angioplasty (J. Am. Coll. Cardiol. 2005 May 17; 45(10): 1723-8; Am. Heart J. 2002 June; 143(6):E5; J. Am. Coll. Cardiol. 1999 May; 33(6):1619-26; Am. J. Cardiol. 77, 31-36 (1996)).

Although it was reported that two-year administration of HMG-CoA RI, plavastatin, after PTCA had reduced the restenosis rate and thus been effective for repression of the cardiovascular events (Am. J. Cardiol. 2000 Oct. 1; 86(7): 742-6) as well as that three- to four-year administration of fluvastatin from immediately after Percutaneous Coronary Artery intervention repressed the onset of the cardiovascular events (JAMA, 2002 Jun. 26; 287(24):3215-22), an improved treatment is expected, which enable more repression of the cardiovascular events.

SUMMARY OF THE INVENTION

In view of the situation that death from the cardiovascular diseases is still a major cause of death, and it is a serious problem that many cardiovascular events are still impossible to prevent by the HMG-CoA RI therapy, an object of the present invention is to provide a composition and/or method for preventing onset and/or recurrence of the cardiovascular events.

In order to solve the problems described above, the inventors of the present invention made an extensive study and found that EPA-E has an effect of preventing onset and/or recurrence of the cardiovascular events, and in particular, an effect of preventing onset and/or recurrence of the cardiovascular events in patients who have escaped the unstable period after cardiovascular angioplasty. The present invention has been thus completed on the basis of such findings. Accordingly, the present invention is directed to:

(1) composition for preventing onset and/or recurrence of cardiovascular events comprising at least EPA-E as its effective component; specifically, (2) composition for preventing onset and/or recurrence of cardiovascular events in a hyperlipidemia patient to whom HMG-CoA RI treatment has been carried out, comprising administrating to the patient the composition containing ethyl icosapentate as its effective component;

(3) method for preventing onset and/or recurrence of cardiovascular events in a patient who has history of acute myocardial infarction, comprising administrating to the patient the composition containing ethyl icosapentate as its effective component;

(4) method for preventing onset and/or recurrence of cardiovascular events in a patient who has escaped the unstable period after cardiovascular angioplasty, comprising administrating to the patient the composition containing ethyl icosapentate as its effective component;

(5) method according to (4), in which the composition starts to be administered after the patient has escaped the unstable period;

(6) method for preventing onset and/or recurrence of cardiovascular events in a patient beyond six months after the cardiovascular angioplasty, comprising administrating to the patient the composition containing ethyl icosapentate as its effective component;

(7) method according to any of (4) to (6), in which the administration of the composition is started beyond six months after the cardiovascular angioplasty and is continued at least for two years;

(8) method according to any of (4) to (7), in which the cardiovascular angioplasty is selected from a group consisting of percutaneous transluminal coronary angioplasty (PTCA), percutaneous transluminal coronary recanalization (PTCR), directional coronary atherectomy (DCA), coronary stent implantation (coronary artery stenting), and coronary artery bypass grafting (AC bypass grafting);

(9) method according to any of (1) to (8), in which the patient suffers from hyperlipidemia;

(10) method according to any of (1) to (9), in which the proportion of the ethyl icosapentate in the total content of fatty acids and derivatives thereof is 96.5% by weight or more;

(11) method according to any of (1) to (10), in which the ethyl icosapentate is orally administered at an amount of 0.3 g/day to 6.0 g/day immediately after meals;

(12) method according to any of (1) to (11), in which the composition is used in combination with an inhibitor for 3-hydroxy-3-methylglutaryl coenzyme A reductase;

(13) method according to (12), in which the inhibitor is pravastatin or simvastatin; and

(14) method according to any of (1) to (13), further comprising DHA-E.

DESCRIPTION OF THE PREFERRED EMBODIMENT

Next, the present invention is described in detail.

A first embodiment of the present invention is a composition and/or a method for preventing onset and/or recurrence of the cardiovascular events which contains EPA-E as its effective component.

Although any composition for prevention of any onset and/or recurrence of cardiovascular events at least containing EPA-E as its effective component is within the scope of this invention, preferred examples include compositions for prevention of cardiovascular death, fatal myocardial infarction, sudden cardiac death, nonfatal myocardial infarction, cardiovascular angioplasty, new onset of rest angina and effort angina, and destabilization of angina pectoris. The subject of the administration of the composition includes all humans requiring prevention of onset of cardiovascular events, and preferred examples include hyperlipidemia patients. While EPA-E content in the total fatty acid and dosage of administration are not particularly limited as long as intended effects of the present invention are attained, high purity EPA-E is preferred; for example, the composition having a proportion of the EPA-E of preferably 40% by weight or more, more preferably 90% by weight or more, and still more preferably 96.5% by weight or more in total of the fatty acids and their derivatives. The daily amount in terms of EPA-E is typically 0.3 to 6.0 g/day. preferably 0.9 to 3.6 g/day, and still more preferably 1.8 to 2.7 g/day.

Other preferable fatty acid contained is any omega-3 unsaturated fatty acid, especially DHA-E. The ratio of EPA-E/DHA-E in the composition, the content of EPA-E and DHA-E in the total fatty acids and administration amount of EPA-E and DHA-E are not limited but the ratio is preferably 0.8 or more, more preferably 1.0 or more, still more preferably 1.2 or more. The composition is preferably highly purified; for example, the proportion of EPA-E+DHA-E in the fatty acids and their derivatives is preferably 40% by weight or more, more preferably 80% by weight or more, and still more preferably 90% or more. The daily amount in terms of EPA-E+DHA-E is typically 0.3 to 10.0 g/day, preferably 0.5 to 6.0 g/day, and still more preferably 1.0 to 4.0 g/day. The low content of other long chain saturated fatty acids is preferred, and among the long chain unsaturated fatty acids, the content of ω-6 fatty acids, and in particular, the content of arachidonic acid is preferably as low as less than 2% by weight, and more preferably less than 1% by weight.

A second embodiment of the present invention is a composition and/or a method for preventing onset and/or recurrence of cardiovascular events of hyperlipidemia patients who is undergoing HMG-CoA RI therapy, which contains at least EPA-E as its effective component. While HMG-CoA RI includes all inhibitors of 3-hydroxy-3-methylglutaryl coenzyme A reductase, a pharmaceutically administrable inhibitor is preferably used, which is preferably pravastatin, simvastatin, lovastatin, fluvastatin, cerivastatin, atorvastatin, pitavastatin, rosuvastatin, and salts and derivatives thereof, and more preferably, pravastatin, lovastatin, simvastatin, fluvastatin, atorvastatin, pitavastatin, or rosuvastatin, and most preferably, pravastatin or simvastatin.

All pharmaceutically administrable salts can be used, and preferred are sodium and potassium salts such as pravastatin sodium, fluvastatin sodium, cerivastatin sodium, atorvastatin calcium, pitavastatin calcium, and rosuvastatin calcium. In the present invention, "pravastatin," for example, also includes the pravastatin in the form of a salt unless otherwise noted.

A third embodiment of the present invention is a composition and/or a method for preventing onset and/or recurrence of cardiovascular events in patients who have history of acute myocardial infarction, which contains at least EPA-E as its effective component.

In the second and third embodiments of the present invention, preferred embodiments of the type of the cardiovascular events, proportion of the EPA-E in the total fatty acid, daily amount, and proportion of other long chain fatty acids are the same as those of the first embodiment of the present invention as described above.

A fourth embodiment of the present invention is a composition and/or a method for preventing onset and/or recurrence of cardiovascular events in patients who have escaped the unstable period after cardiovascular angioplasty, which contains at least EPA-E as its effective component. The patients who underwent cardiovascular angioplasty have a high possibility to show the symptoms due to the cardiovascular angioplasty itself within about six months and a higher possibility within about three months, after the cardiovascular angioplasty. This period is referred to as the unstable period in this specification. Therefore, a fourth embodiment of the present invention is preferably a composition for preventing onset and/or recurrence of cardiovascular events in patients beyond six months after the cardiovascular angioplasty. Thus the cardiovascular events such as restenosis during the unstable period, which are caused by the cardiovascular angioplasty itself, are excluded from the scope of this invention. The type of the cardiovascular angioplasty is not particularly limited, and examples include percutaneous transluminal coronary angioplasty (hereinafter abbreviated as PTCA), percutaneous transluminal coronary recanalization (hereinafter abbreviated as PTCR), directional coronary atherectomy (hereinafter abbreviated as DCA), coronary stent implantation (coronary artery stenting), and coronary artery bypass grafting (hereinafter abbreviated as AC bypass grafting).

A fifth embodiment of the present invention is a composition and/or a method for preventing onset and/or recurrence of cardiovascular events in patients who have escaped the unstable period after cardiovascular angioplasty, which contains at least EPA-E as its effective component, and preferably a composition for preventing onset and/or recurrence of cardiovascular events in patients beyond six months after the cardiovascular angioplasty.

The composition according to the fourth and fifth embodiments is administered to the patients who have escaped the unstable period after cardiovascular angioplasty and preferably to the patients beyond six months after the cardiovascular angioplasty.

The cardiovascular events that occur after the unstable period are thought to generate by a mechanism which is different from that of the cardiovascular events such as restenosis during the unstable period, which are caused by the cardiovascular angioplasty itself. The rate of the cardiovascular events that occur after the unstable period is relatively high. The composition according to the fourth and fifth embodiments is administered after the unstable period, specifically beyond after cardiovascular angioplasty. The composition is preferable to be administered continuously for a long time, specifically for two years or more, more preferably for three years and a half or more, still more preferably for five years or more and thus is effective for preventing onset and/or recurrence of cardiovascular events which occur after the unstable period.

While EPA-E content in the total fatty acid and dosage of the compositions according to the fourth and fifth embodiments of the present invention are not particularly limited as long as the composition contains EPA-E as its effective component and intended effects of the present invention are attained, high purity EPA-E is preferably used; for example, the composition having a proportion of the EPA-E of preferably 40% by weight or more, more preferably 90% by weight or more, and still more preferably 96.5% by weight or more in total of the fatty acids and their derivatives. The daily amount in terms of EPA-E is typically 0.3 to 6 g/day, preferably 0.9 to 3.6 g/day, and still more preferably 1.8 to 2.7 g/day.

Other preferable fatty acid contained is any omega-3 unsaturated fatty acid, especially DHA-E. The ratio of EPA-E/DHA-E in the composition, the content of EPA-E and DHA-E in the total fatty acids and administration amount of EPA-E and DHA-E are not limited but the ratio is preferably 0.8 or more, more preferably 1.0 or more, still more preferably 1.2 or more. The composition is preferably highly purified; for example, the proportion of EPA-E+DHA-E in the fatty acids and their derivatives is preferably 40% by weight or more, more preferably 80% by weight or more, and still more preferably 90% or more. The daily amount in terms of EPA-E+DHA-E is typically 0.3 to 10.0 g/day, preferably 0.5 to 6.0 g/day, and still more preferably 1.0 to 4.0 g/day. The low content of other long chain saturated fatty acids is preferred, and among the long chain unsaturated fatty acids, the content of $\omega$-6 fatty acids, and in particular, the content of arachidonic acid is preferably as low as less than 2% by weight, and more preferably less than 1% by weight.

The compositions according to the first to fifth embodiments of the present invention have the effect of preventing onset and/or recurrence of cardiovascular events when orally administered to a normal person, a person suffering from hyperlipidemia, diabetes or hypertension with the risk of cardiovascular events, or a patient to whom HMG-CoA RI treatment has been carried out, although those whom the compositions are administered are not limited thereto. The composition of the present invention also has a combined effect when used with HMG-CoA RI, and accordingly, onset and/or recurrence of the cardiovascular events can be even more effectively prevented by using in combination with the HMG-CoA RI.

The compositions of the present invention contain a smaller amount of impurities such as saturated fatty acids and arachidonic acid, which are unfavorable for cardiovascular events, than fish oil or fish oil concentrate, and intended effects can be attained without causing problems like overnutrition or excessive intake of vitamin A. In addition, since the effective form of the present composition is an ester, which is more stable to oxidation than that in fish oil in which its effective form is a triglyceride, a sufficiently stable composition can be produced by adding a conventional antioxidant. Thus the use of the EPA-E has enabled production of a composition for preventing onset and/or recurrence of cardiovascular events which can be used in clinical practice.

In the present invention, the term "icosapentaenoic acid" designates all-cis-5,8,11,14,17-icosapentaenoic acid.

In the present invention, the term "cardiovascular events" is used to generally refer to pathological changes of cardiovascular system, and includes cardiovascular death (fatal myocardial infarction and sudden cardiac death), nonfatal myocardial infarction, cardiovascular angioplasty (PTCA, PTCR, DCA, coronary stent implantation (coronary artery stenting), and AC bypass grafting), new onset of rest angina or effort angina, and destabilization of angina pectoris (hospitalization, and PTCA, PTCR, DCA, coronary stent implantation (coronary artery stenting), AC bypass grafting, or other cardiovascular angioplasty).

In the present invention, the term "hyperlipidemia patient" designates the patient experiencing increase in serum T-Cho concentration, increase in serum LDL-Cho concentration, decrease in serum HDL-Cho concentration, or increase in serum TG. In the narrow sense, the term "hyperlipidemia patient" designates, a patient who suffers from any one of hypercholesterolemia (with the serum T-Cho concentration of about 220 mg/dl or higher, and in the narrower sense, with the serum T-Cho concentration of 250 mg/dl or higher), hyper-LDL cholesterolemia (with the serum LDL-Cho concentration of 140 mg/dl or higher), hypo-HDL cholesterolemia (with the serum HDL-Cho concentration of less than 40 mg/dl) and hypertriglyceridemia (with the serum TG of 150 mg/dl or higher).

In the present invention, the term "use in combination with HMG-CoA RI" includes both the embodiment in which the composition containing EPA-E as its effective component and the HMG-CoA RI are simultaneously administered and the embodiment in which both agents are separately administered. When these agents are simultaneously administered, they may be formulated either as a combination drug, or separate drugs. When these agents are separately administered, the composition containing EPA-E as its effective component may be administered either before or after the HMG-CoA RI. The administration amount and ratio of the composition containing EPA-E as its effective component and the HMG-CoA RI may be adequately selected. Preferable examples of use of HMG-CoA RI which is administered in combination is the similar to those shown in the second embodiment as example.

The compositions and/or methods according to the first to fifth embodiments of the present invention has the action of preventing onset and/or recurrence of the cardiovascular events by sole administration of the composition, and in particular, the present composition is expected to exert an effect of preventing onset and/or recurrence of the cardiovascular events which cannot be prevented by administration of the HMG-CoA RI. In addition, EPA-E has not only the action of reducing the serum T-Cho concentration and the serum TG, but also the action of suppressing platelet aggregation based on inhibition of arachidonic acid cascade, which is a pharmacological action different from the HMG-CoA RI. Therefore, the stronger action of preventing onset and/or recurrence of the cardiovascular events of the present composition can be exerted by using in combination with the HMG-CoA RI.

The compositions according to the first to fifth embodiments of the present invention can include pharmaceutically accepted carriers as well as its effective component. Since EPA-E and DHA-E are highly unsaturated, inclusion of an effective amount of an antioxidant such as butylated hydroxytoluene, butylated hydroxyanisole, propyl gallate, gallic acid, and pharmaceutically acceptable quinone, and α-tocopherol is preferable.

The preparation may be orally administered to the patients in the dosage form of tablet, capsule, microcapsule, granules, fine granules, powder, oral liquid preparation, syrup, or jelly. Preferably, the preparation is filled in a capsule such as soft capsule or microcapsule and is orally administered.

It is to be noted that high purity EPA-E soft capsule (Epadel™ and Epadel S™) are commercially available in Japan as safe therapeutic agents for arteriosclerosis obliterans and hyperlipidemia with reduced side effects, and the proportion of EPA-E in the total fatty acid is at least 96.5% by weight. Further, soft capsule (Omacor™, Ross products) containing about 46% by weight of EPA-E and about 38% by weight of DHA-E is commercially available in the U.S. and other countries as a therapeutic agent for hypertriglyceridemia. These drugs may be purchased for use in the present invention.

The amount and period for administration of the composition for preventing onset and/or recurrence of the cardiovascular events of the present invention should be sufficient for the expression of the intended action and may be adequately adjusted depending on the dosage form, administration route, frequency, severity of the symptoms, body weight, age, and the like. When orally administered, the composition may be administered at an amount of 0.3 to 6 g/day, preferably 0.9 to 3.6 g/day, and more preferably 1.8 to 2.7 g/day in terms of EPA-E, and while the composition is typically administered in 3 doses, the total amount may optionally be administered in a single dose or in a few doses. The composition is preferably administered during or after the meal, and more preferably, immediately (within 30 minutes) after the meal. When such an amount of the composition is orally administered, the administration period is typically at least one year, preferably at least two years, more preferably at least three years and a half, and further more preferably at least five years. The administration is preferably continued as long as there is a considerable risk of onset and/or recurrence of the cardiovascular events. If necessary, drug holidays of about one day to three months, and preferably about one week to one month may be given.

The HMG-CoA RI that is used in combination with the composition according to the first to fifth embodiments of the present invention is preferably used according to the recommended administration procedure and the drug type, and the dosage form, administration method, frequency per day may be adequately adjusted depending on severity of the symptoms, body weight, sex, age, and the like. When orally administered, the HMG-CoA RI is typically administered 1 or two times per day at 0.05 to 200 mg/day, and preferably 0.1 to 100 mg/day, and the total amount may optionally be administered in a few doses. The amount may be reduced according to the administration amount of EPA-E.

It is to be noted that pravastatin sodium (Mevalotin™ tablets and fine granules, Sankyo Co., Ltd.), simvastatin (Lipovas™ tablets, Banyu Pharmaceutical Co., Ltd.), fluvastatin sodium (Lochol™ tablets, Novartis Pharma K.K. and Tanabe Seiyaku Co., Ltd.), atorvastatin calcium hydrate (Lipitor™ tablets, Astellas Pharma Inc. and Pfizer), pitavastatin calcium (Livalo™ tablets, Kowa Company, Ltd. and Sankyo Co., Ltd., and rosuvastatin calcium (Crestor™ tablets, AstraZeneca K.K. and Shionogi & Co., Ltd.) are commercially available in Japan as drugs for treating hyperlipidemia, and lovastatin (Mevacor™ tablets, Merck) is commercially available in the U.S. as a drug for treating hyperlipidemia. These drugs may be purchased and used according to the directions recommended by the manufacturer. Optionally, at least two of these drugs can be combined and used together.

The preferable daily amount are, for example, 5-60 mg or preferably 10-20 mg for pravastatin sodium, 2.5-60 mg or preferably 5-20 mg for simvastatin, 10-180 mg or preferably 20-60 mg for fluvastatin sodium, 5-120 mg or preferably 10-40 mg for atorvastatin calcium hydrate, 0.5-12 mg or preferably 1-4 mg for pitavastatin calcium, 1.25-60 mg or preferably 2.5-20 mg for rosuvastatin calcium, 5-160 mg or preferably 10-80 mg for lovastatin, and 0.075-0.9 mg or preferably 0.15-0.3 mg for cervastatin but not limited to them.

The compound of the first to fifth embodiments is used in combination with at least one appropriately selected, according to the condition of the patient, from a group including anti-platelet drugs such as Aspirin, Ticlopidin, clopidogrel, and cilostazol; anticoagulation drugs such as warfarin, heparin, and ximelagatran; angiotensin ii receptor competitor such as candesartan, and losartan; andiotensin-converting enzyme inhibitor; calcium channel competitor such as amlodipin and cilnidipin; antihypertensive such as α1 blocker; α glucosidase inhibitor such as voglibose and akarbose; biganide group; thiazolidindion-type such as pioglitazone, rosiglitazone, and riboglitazone; diabetic agent or glucose tolerance improving drug such as quick-acting insulin secreting secretagogue (e.g., mitiglinide and nateglinide); and anti-hyperlipidemic drug such as HMG-CoA RI (described above), fibrate drug, squalene synthetase inhibitor (e.g., tak-475), cholesterol absorption inhibitor (e.g., ezetimibe).

The composition according to the first to fifth embodiments of the present invention can be used in a package in combination with at least one drug such as HMG-CoA RI and others.

EXAMPLES

Next, the effects of the present composition are shown with Experiments and Examples, which by no means limit the scope of the present invention.

Experiment 1 (Long Term Preventive Action of EPA-E on the Onset of Cardiovascular Events)

Test Procedure

A five-year long term observation of onset and/or recurrence of the cardiovascular events was conducted by administering EPA-E to hyperlipidemia patients exhibiting a serum T-Cho concentration of 250 mg/dl or higher, including males at the age of 40 to 75 and postmenopausal females at the age of 75 or younger. The observation was conducted by a large scale randomized unblinded controlled trial of the EPA-E group (9,326 cases) and the control group (9,319 cases). The patients were randomized into the groups at the beginning of the trial so that no significant difference is found between the groups in the background factors of the patients, namely, age, sex ratio, history and complication, type and proportion of the HMG-CoA RI, serum lipid concentration, and the like. The patients of both groups were under nutritional counseling, and HMG-CoA RI was administered to them as a base drug.

The data was collected from 18,465 participant patients by about 4,900 participant physicians in about 2,900 participant facilities with sufficient case number, randomization, and the strictness required for the controlled trial. For example, in choosing the participant patients, the serum T-Cho concentration was measured twice at an interval of two to four weeks except for the cases where the patients underwent an adequate nutritional consulting with high compliance and the cases where the fasting blood was collected after cessation of the antilipidemic drug, in which the measurement was conducted only once. While untreated patients were preferable, in the case of patients who had been taking an antilipidemic drug for more than six months at the start of the trial, four weeks of drug holidays (eight weeks in the case of probucol) were given. Patients who were administered with the antilipidemic drug for six months or less at the start of the trial were admitted in the trial with no drug holiday, and when the drug was HMG-CoA RI, its administration was continued while other drugs were changed to HMG-CoA RI.

In order to exclude cardiovascular events in the unstable period after the onset of myocardial infarction and cardiovascular events such as restenosis in the unstable period which is conceived to be caused by the angioplasty itself, the patients at or within six months after the acute myocardial infarction and patients at or within six months after the cardiovascular angioplasty were excluded from the trial subjects, and only patients who are beyond six months after such events and who are conceived to be in the stable period were included in the trial. In addition, patients who are inadequate for the examination of the action of preventing the onset of cardiovascular events for a long time which is the object of this trial, for example, patients of unstable angina pectoris, patients with history or complication of serious heart diseases (such as severe arrhythmia, heart failure, cardiomyopathy, valvular disease, and congenital heart disease), patients at or within six months from the onset of cerebrovascular disorder, and patients with complication of serious liver disease or kidney disease, as well as the patients whose participation was judged to be inappropriate by the attending physician were excluded from the trial.

Epadel (Mochida Pharmaceutical Co., Ltd.) was orally administered as EPA-E typically at an adult dose of 600 mg after the meal three times a day. In the case of abnormal serum TG, however, the dose could be increased to 900 mg per administration and three times a day.

Pravastatin sodium (Mevalotin tablets and fine granules, Sankyo Co., Ltd.), simvastatin (Lipovas tablets, Banyu Pharmaceutical Co., Ltd.), or atorvastatin calcium hydrate (Lipitor tablets, Astellas Pharma Inc. and Pfizer) was used for the HMG-CoA RI, and these drugs were orally administered according to the predetermined dosage regimen.

For five years from before the start of the trial to the end of the trial, the concentration of the serum lipid (T-Cho, HDL-Cho, and TG) was periodically measured, and LDL-Cho was calculated by the equation of T-Cho-HDL-Cho-(TG/5). In addition, onset of cardiovascular events (cardiovascular death (fatal myocardial infarction and sudden cardiac death), non-fatal myocardial infarction, cardiovascular angioplasty, new onset of rest angina or effort angina, and destabilization of angina pectoris (hospitalization and cardiovascular angioplasty)) was observed.

It is to be noted that this trial was consistent with "Good Post Marketing Surveillance Practice (GPMSP)" and "Good Clinical Practice (GCP)," and was conducted under trial organization with a trial director. Before the trial was started, the content of the trial was explained to the patients, and the patients participated in the trial on their own free will with informed consent.

Results

In the observation period of five years, the serum T-Cho, LDL-Cho, and TG concentrations decreased in both groups, and no significant change in the serum HDL-Cho concentration was noted. In particular, decrease in the serum TG concentration was more significant in the EPA-E group.

The number of incidence and incidence rate (%) of the cardiovascular events, and the odds ratio calculated for the EPA-E group in relation to the control group in the observation period of five years are shown in Table 1. The odds ratio was calculated by the equation of (incidence rate of the EPA-E group)/(incidence rate of the control group), and the inhibition rate of onset of the cardiovascular events was calculated by the equation of {(incidence rate of the cardiovascular events of the control group-incidence rate of the cardiovascular events of the EPA-E group)/incidence rate of the cardiovascular events of the control group}×100.

TABLE 1

| Patient groups categorized by background factor | | Control group Cases with the cardiovascular events/all cases (incidence rate, %) | EPA-E group Cases with the cardiovascular events/all cases (incidence rate, %) | Odds ratio |
|---|---|---|---|---|
| All Cases | | 324/9,319 (3.48) | 262/9,326 (2.81) | 0.808 |
| Myocardial Infarction | No | 223/8,817 (2.53) | 180/8,778 (2.05) | 0.811 |
| | Yes | 101/502 (20.12) | 82/548 (14.96) | 0.744 |
| Cardiovascular angioplasty | No | 215/8,813 (2.44) | 185/8,793 (2.10) | 0.862 |
| | Yes | 109/506 (21.54) | 77/533 (14.45) | 0.671 |

As a result of EPA-E administration, the incidence rate of the cardiovascular events over five years in relation to all cases reduced to 2.81% compared to the incidence rate of the cardiovascular events in the control group of 3.48%. The odds ratio was 0.808, and the EPA-E administration reduced the incidence rate of the cardiovascular events by about 19% compared to the control group.

Accordingly, the effect of preventing onset and/or recurrence of the cardiovascular events by the EPA-E administration was demonstrated.

In the cases of the patients with history of myocardial infarction and the patients with history of cardiovascular angioplasty, the incidence rates of the cardiovascular events in the control group were 20.12% and 21.54%, respectively, and the incidence rates of the cardiovascular events were significantly higher than the incidence rates of the cardiovascular events in the patients with no history of myocardial infarction and the patients with no history of cardiovascular angioplasty which were 2.53% and 2.44%, respectively. In the meanwhile, as a result of the EPA-E administration, the odds ratio was 0.744 in the patients with history of myocardial infarction and 0.671 in the patients with history of cardiovascular angioplasty, which were significantly lower than 0.811 in the patients with no history of myocardial infarction and 0.862 in the patients with no history of cardiovascular angioplasty; and accordingly, the EPA-E administration resulted in the decrease of the incidence rate of the cardiovascular events by about 26% in the patients with history of myocardial infarction and about 33% in the patients with history of cardiovascular angioplasty compared to the control group.

From the results as described above, the significant effect of the EPA-E administration in preventing onset of the cardiovascular events was demonstrated for the patients with history of myocardial infarction and the patients with history of cardiovascular angioplasty.

INDUSTRIAL APPLICABILITY

The composition of the present invention which contains EPA-E, or contains at least EPA-E as its effective component, is useful in preventing onset and/or recurrence of the cardiovascular events. In particular, the composition and/or method of the present invention is useful in preventing onset and/or recurrence of the cardiovascular events of hyperlipidemia patients or hyperlipidemia patients who have been treated with HMG-CoA RI.

The composition and/or methods of the present invention is expected to prevent onset and/or recurrence of the cardiovascular events of patients who have escaped the unstable period after cardiovascular angioplasty.

When the composition of the present invention is used in combination with an HMG-CoA RI, the action is further synergistically enhanced, and such a use is expected to further improve the effect for preventing onset and/or recurrence of the cardiovascular events in patients who have experienced the cardiovascular events, especially patients beyond six months after the cardiovascular angioplasty. Accordingly, such use of the present composition with the HMG-CoA RI is clinically favorable.

What is claimed:

1. A method for reducing risk of onset and/or recurrence of cardiovascular events in a patient who has escaped the unstable period after cardiovascular angioplasty,
   comprising starting to administer a composition to the patient after the patient has escaped the unstable period,
   wherein said composition contains ethyl icosapentate as an effective component;
   wherein the proportion of the ethyl icosapentate in the total content of fatty acids or derivatives thereof is 96.5% by weight or more, and
   wherein the cardiovascular event is selected from the group consisting of cardiovascular death, myocardial infarction, cardiovascular angioplasty, new onset of rest angina, new onset of effort angina, and destabilization of angina pectoris.

2. A method for reducing risk of onset and/or recurrence of cardiovascular events in a patient after six months have passed since cardiovascular angioplasty,
   comprising starting to administer a composition to the patient after six months have passed since the cardiovascular angioplasty,
   wherein said composition contains ethyl icosapentate as an effective component;
   wherein the proportion of the ethyl icosapentate in the total content of fatty acids or derivatives thereof is 96.5% by weight or more, and
   wherein the cardiovascular event is selected from the group consisting of cardiovascular death, myocardial infarction, cardiovascular angioplasty, new onset of rest angina, new onset of effort angina, and destabilization of angina pectoris.

3. The method according to claim 1, wherein the patient suffers from hyperlipidemia.

4. The method according to claim 1, wherein the amount of ethyl icosapentate in the composition is orally administered at an amount of 0.3 g/day to 6.0 g/day.

5. The method according to claim 1, wherein said composition further contains other fatty acids or derivatives thereof.

6. The method according to claim 1, wherein the cardiovascular angioplasty is selected from the group consisting of percutaneous transluminal coronary angioplasty (PTCA), percutaneous transluminal coronary recanalization (PTCR), directional coronary atherectomy (DCA), coronary stent implantation (coronary artery stenting), and coronary artery bypass grafting (AC bypass grafting).

7. The method of claim 1, wherein said patient has received percutaneous transluminal coronary angioplasty (PTCA).

8. The method according to claim 1, wherein the composition starts to be administered to the patient later than six months after the cardiovascular angioplasty.

9. The method according to claim 1, wherein the composition is administered to the patient for at least one year.

10. The method according to claim 1, wherein the composition is administered to the patient for at least two years.

11. The method according to claim 4, wherein the amount of ethyl icosapentate in the composition is orally administered at an amount of 0.9 to 3.6 g/day.

12. The method according to claim 4, wherein the amount of ethyl icosapentate in the composition is orally administered at an amount of 1.8 to 2.7 g/day.

13. The method according to claim 3, wherein the hyperlipidemic patient has a serum triglyceride of 150 mg/dl or higher.

14. The method according to claim 1, wherein the composition is in the form of a capsule.

15. A method for reducing the incidence rate of a cardiovascular event in a group of patients who have escaped the unstable period after cardiovascular angioplasty, comprising starting to administer a composition to the patient after the patient has escaped the unstable period, wherein said composition comprises ethyl icosapentate as an effective component;

wherein the proportion of the ethyl icosapentate in the total content of fatty acids or derivatives thereof is 96.5% by weight or more, and wherein the cardiovascular event is selected from the group consisting of cardiovascular death, myocardial infarction, cardiovascular angioplasty, new onset of rest angina, new onset of effort angina, and destabilization of angina pectoris.

\* \* \* \* \*